United States Patent
Paulsen

(10) Patent No.: US 6,225,348 B1
(45) Date of Patent: May 1, 2001

(54) METHOD OF TREATING MACULAR DEGENERATION WITH A PROSTAGLANDIN DERIVATIVE

(76) Inventor: Alfred W. Paulsen, 706 W. 8th, Gillette, WY (US) 82716

( * ) Notice: Subject to any disclaimer, the term of this patent is extended or adjusted under 35 U.S.C. 154(b) by 0 days.

(21) Appl. No.: 09/377,561

(22) Filed: Aug. 19, 1999

Related U.S. Application Data

(60) Provisional application No. 60/097,204, filed on Aug. 20, 1998.

(51) Int. Cl.$^7$ .................................................. A61K 31/215
(52) U.S. Cl. ............................ 514/530; 514/573; 514/912
(58) Field of Search .................................... 514/530, 573, 514/912

(56) References Cited

U.S. PATENT DOCUMENTS

| | | |
|---|---|---|
| 5,466,833 | 11/1995 | Ivanics et al. . |
| 5,510,383 | 4/1996 | Bishop et al. . |
| 5,770,589 | 6/1998 | Billson et al. . |
| 5,886,035 | 3/1999 | Shirasawa et al. . |
| 5,891,847 | 4/1999 | Naveh . |
| 5,905,091 | 5/1999 | Fuller . |

FOREIGN PATENT DOCUMENTS

| | | |
|---|---|---|
| WO 90/02553 | 3/1990 | (WO) . |
| WO 93/00329 | 1/1993 | (WO) . |

OTHER PUBLICATIONS

Pharmacia & Upjohn, "Xalatan Drug Insert", Brochure, Jun. 3, 1996, Pharmacia, Inc., Kalamazoo, MI 49001, USA.

*Primary Examiner*—Zohreh Fay
(74) *Attorney, Agent, or Firm*—Dorr, Carson, Sloan & Birney, P.C.

(57) ABSTRACT

A method of treating age-related macular degeneration in an eye is described, comprising contacting the eye with a therapeutic amount of a prostaglandin $F_{2\alpha}$ derivative. The preferred prostaglandin $F_{2\alpha}$ derivative is latanoprost, and the preferred dosage is between about 1.5 $\mu$g and about 4.5 $\mu$g per day per eye.

9 Claims, 1 Drawing Sheet

METHOD OF TREATING MACULAR DEGENERATION WITH A PROSTAGLANDIN DERIVATIVE

CROSS REFERENCE TO RELATED APPLICATIONS

This application claims the benefit of U.S. Provisional Application Ser. No. 60/097,204, filed Aug. 20, 1998. This application further makes reference to Document Disclosure 425241, dated Oct. 6, 1997.

BACKGROUND OF THE INVENTION

1. Field of the Invention

The present invention relates to the treatment of retinal diseases, and more particularly, to the treatment of macular degeneration with prostaglandin derivatives.

2. Statement of the Problem

In the retina, the macula lutea, or macula retinae, is a small, irregular, yellowish area about three degrees wide, or less than 1 $mm^2$. The macula lutea lies slightly lateral to the area in the center of the retina that constitutes the region of maximum visual acuity. This area is made up almost wholly of retinal cones and is important for color vision.

The major cause of blindness in people over the age of sixty in the United States is age-related macular degeneration. Macular degeneration results in a loss of central vision in both eyes in a typically slow process with continuous progressive loss of the vision. The visual loss is produced by pathological changes in the macula lutea. Macular degeneration is characterized by spots of pigmentation (druscen) or other abnormalities. The disease has a genetic factor.

The incidence of macular degeneration decreases in relationship to the darkness of eye color. Macular degeneration almost never afflicts African-Americans, and it occurs much less often in individuals with brown irises. The greatest frequency is found in persons with blue irises.

Macular degeneration is conveniently divided into three stages. It may present as early stage macular degeneration. At least 20% of patients develop an active neurovascular form.

One end stage of this condition is known as atrophic macular degeneration or "dry" macular degeneration, while a second end stage is known as neovascular macular degeneration or "wet" macular degeneration, which is caused when new blood vessels begin to grow under the retina, particularly the macula.

There are no effective treatments for dry macular degeneration.

Wet macular degeneration is treated by various methods, for example, laser treatment. However, a complication of laser treatment is actual loss of vision. In addition, laser treatment, where applicable, is not always a permanent cure since the blood vessels may begin to grow again.

Another type of treatment for wet macular degeneration involves injecting a photo-activated chemical into the general circulation of the patient and then exposing the patient to light, activating the chemical, which then kills the overgrowing blood vessels. This treatment has the unwanted side effect of making the patient extremely sensitive to light.

Anti-angiogenesis therapy has also been attempted as a treatment for wet macular degeneration. Because of the preliminary nature of these experiments, it is not yet known whether this treatment will be effective.

A surgical treatment of macular degeneration involves rotating the retina away from the area of blood vessel growth. Another surgical treatment involves performing a retinal cell transplant. These treatments subject the patient to surgical insult, and neither has been shown to be effective in preventing continuing degeneration of the macula.

A recent study has indicated that foods rich in carotenoids, especially lutein and zeaxanthin, the only pigments found in the macula lutea, may protect against the development of macular degeneration. Other treatments that have been attempted to prevent or treat macular degeneration include the use of vitamins A and E. None of these other treatments with anti-oxidants has been shown to be effective in the treatment or prevention of macular degeneration.

Thus, although age-related macular degeneration is the most prevalent cause of blindness in the elderly population in developed countries, there is no effective treatment that delays the course of or prevents the development of macular degeneration.

Prostaglandin derivatives have been used for some time to treat ocular hypertension (glaucoma). One of these derivatives, latanoprost, is a prostaglandin $F_{2\alpha}$ derivative. The chemical name of latanoprost is isopropyl-(Z)-7[(1R,2R,3R,5S)3,5-dihydroxy-2-[(3R)-3-hydroxy-5-phenylpentyl]cyclo-pentyl]-5-heptenoate. The molecular formula is $C_{26}H_{40}O_5$ and the molecular weight is 432.58. The chemical structure is illustrated in FIG. 1. The chemical structure of latanoprost is disclosed in PCT WO 90/02553, and a process for making latanoprost is disclosed in PCT WO 93/00329. A novel process for making latanoprost is taught in U.S. Pat. No. 5,466,833 to Ivanics et al., and the use of latanoprost in treating glaucoma is disclosed in U.S. Pat. No. 5,510,383 to Bishop et al.

It is also known that prostaglandin $F_{2\alpha}$ derivatives have the ability to stimulate melanogenesis in tissues to which they are applied (see, for example, U.S. Pat. No. 5,905,091 to Fuller). For example, the application of latanoprost to the eye during the treatment of glaucoma often results in increased pigmentation of the eye, that is, in light-colored eyes with blue irises, the irises can become brown. This effect of prostaglandin $F_{2\alpha}$ derivatives is discussed in the drug insert for the XALATAN™ latanoprost ophthalmic solution from Pharmacia & Upjohn This melanogenistic property has been seen as a negative side effect of the use of prostaglandin $F_{2\alpha}$ derivatives, and it is suggested that XALATAN™ treatment be discontinued if increased pigmentation ensues during treatment (XALATAN™ drug insert). Solutions to overcome this problem are discussed in U.S. Pat. No. 5,886,035 to Shirasawa et al.

Solution to the Problem.

The present invention discloses a method of treating age-related macular degeneration with prostaglandin $F_{2\alpha}$ derivatives, and preferably with latanoprost. This method is based on the property of prostaglandin $F_{2\alpha}$ derivatives discussed above in which these derivatives cause the iris and other tissues to darken when applied topically to the eye.

SUMMARY OF TITLE INVENTION

This invention provides a method of treating age-related macular degeneration with prostaglandin $F_{2\alpha}$ derivatives, such as 13,14-dihydro-15(R)-17-phenyl-18,19,20-trinor-$PGF_{2\alpha}$ esters, and preferably with latanoprost (isopropyl-(Z)-7[(1R,2R,3R,5S) 3,5-dihydroxy-2-[(3R)-3-hydroxy-5-phenyl pentyl]cyclo-pentyl]-5-heptenoate).

In the method of the present invention, an ophthalmic solution containing a prostaglandin $F_{2\alpha}$ derivative, such as latanoprost, is applied to the affected eye or eyes once daily at a dosing level of approximately one drop (about 1.5 $\mu$g of derivative) to approximately three drops (about 4.5 $\mu$g of derivative) per day per eye.

It is an object of the present invention to prevent macular degeneration and to halt or reverse the effects of macular degeneration by the application of prostaglandin $F_{2\alpha}$ derivatives, and preferably latanoprost, to affected eyes.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
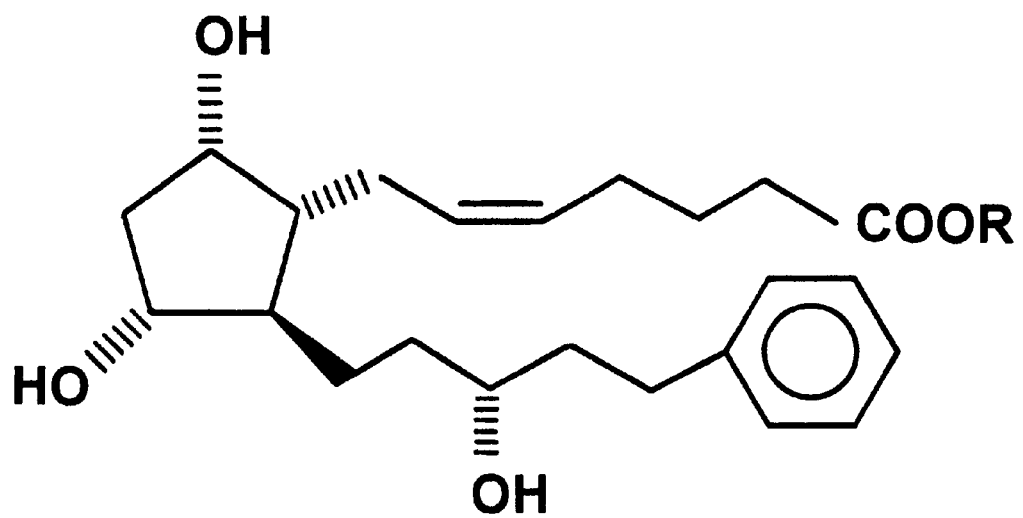
FIG. 1 is an illustration of the chemical structure of 13,14-dihydro-15(R)-17-phenyl-18,19,20-trinor-PGF$_{2\alpha}$ isopropyl ester, where R is a saturated or unsaturated straight, branched, or cyclic C$_{1-7}$ alkyl or phenyl or benzyl group.

Prostaglandin derivatives have been used for some time to treat ocular hypertension (glaucoma). In particular, the prostaglandin F$_{2\alpha}$ derivatives illustrated in FIG. 1 and having the formula 13,14-dihydro-15(R)-17-phenyl-18,19,20-trinor-PGF$_{2\alpha}$ isopropyl ester, where R is a saturated or unsaturated straight, branched, or cyclic C$_{1-7}$ alkyl or phenyl or benzyl group, have been found to be particularly efficacious.

Figure 2:
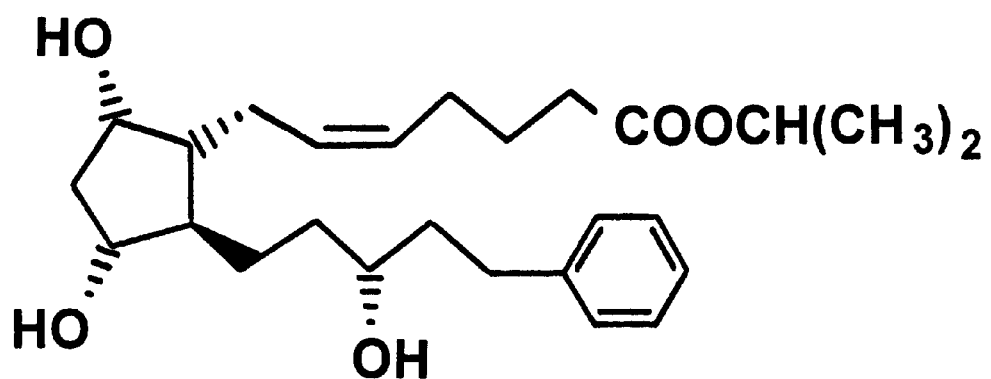
FIG. 2 is an illustration of the chemical structure of latanoprost.

One of the prostaglandin F$_{2\alpha}$ derivatives derived from 13,14-dihydro-15(R)-17-phenyl-18,19,20-trinor-PGF$_{2\alpha}$ isopropyl ester is latanoprost. The chemical name of latanoprost is isopropyl-(Z)-7[(1R,2R,3R,5S)3,5-dihydroxy-2-[(3R)-3-hydroxy-5-phenylpentyl]cyclo-pentyl]-5-heptenoate. The molecular formula is C$_{26}$H$_{40}$O$_5$ and the molecular weight is 432.58. The chemical structure of latanoprost is shown in FIG. 2.

One of the side effects of latanoprost treatment for glaucoma is a gradual change in eye color. This change in eye color occurs over a period of months to years. This change is effected by an increase in the amount of brown pigment in the iris, as a result of an increase in the number of melanosomes (pigment granules) in the melanocytes due to stimulation by latanoprost of melanin production in the melanocytes (melanogenesis). Typically the brown pigmentation will begin around the pupil and spread concentrically toward the periphery of the iris; however, the entire iris or parts thereof may become brownish. The increased pigmentation may be permanent.

It is Applicant's unique discovery and the key to the present invention that using latanoprost to darken the color of the eye may have an effect on macular degeneration. That is, the action of latanoprost in changing lighter eye color pigments to darker pigments may prevent, slow down, arrest, reverse, or otherwise mitigate the progression of the ocular disease macular degeneration. This is based on the above-described finding that people with darker irises show a decreased incidence of macular degeneration.

Thus, the present invention contemplates the introduction of prostaglandin derivatives into the eye to treat macular degeneration by causing melanogenesis in the eye structures. It is preferable to use prostaglandin F$_{2\alpha}$ derivatives of the chemical structure 13,14-dihydro-15(R)-17-phenyl-18, 19,20-trinor-PGF$_{2\alpha}$ isopropyl ester, where R is a saturated or unsaturated straight, branched, or cyclic C$_{1-7}$ alkyl or phenyl or benzyl group. Of such derivatives, latanoprost, having the chemical structure isopropyl-(Z)-7[(1R,2R,3R,5S)3,5-dihydroxy-2-[(3R)-3-hydroxy-5-phenyl pentyl] cyclopentyl]-5-heptenoate, is of greatest interest.

A preferred method of the present invention for treating macular degeneration consists of contacting the eye with a therapeutically effective amount of an aforesaid prostaglandin F$_{2\alpha}$ derivative in an acceptable ophthalmic solution. A therapeutically effective amount is an amount of the active agent that is effective in achieving the desired therapeutic effect. The therapeutically effective amount depends on the administration regimen, the condition of the treated individual, etc. as known per se.

The invention further relates to the use of therapeutically active and physiologically acceptable prostaglandin F$_{2\alpha}$ derivatives as defined above for the preparation of an ophthalmologic compositions for the treatment of macular degeneration. That is, the prostaglandin F$_{2\alpha}$ derivatives are mixed with a conventional ophthalmologically compatible vehicle, for example, aqueous solutions such as physiological salines, oil solutions, or ointments. The vehicle may contain ophthalmologically compatible preservatives such as benzalkonium chloride, surfactants such as polysorbate 80, liposomes, or polymers such as methylcellulose, polyvinyl alcohol, polyvinyl pyrrolidone and hyaluronic acid, which may be used for increasing the viscosity.

The active agent may be administered in a number of ways. By one mode of administration, said active agent is applied topically onto the eye. For topical application, said active agent may be formulated with a vehicle that is compatible with the eye and preferably such that facilitates penetration of said active agent into the eye. For such mode of application, said active agent may be formulated in the form of eyedrops (in which the active agent is dissolved in a physiological solution), in the form of ointments, in the form of a liposome solution, etc.

In a highly preferred embodiment of the present invention, the prostaglandin derivative latanoprost is used as the active agent. To use latanoprost to mitigate the progression of macular degeneration, an ophthalmic solution ranging from about 0.005% (50 μg/ml) to about 0.025% (250 μg/ml) of latanoprost is preferred. Latanoprost is marketed as such an ophthalmic solution in the form of eyedrops under the trade name XALATAN™ (trademark) by Pharmacia Inc., Kalamazoo, Mich. 49001, USA. This solution also contains 0.02% benzalkonium chloride as a preservative, and the inactive ingredients sodium chloride, sodium dehydrogen phosphate monohydrate, disodium hydrogen phosphate anhydrous, and water. Each milliliter of XALATAN™ solution contains 50 micrograms (50 μg) of latanoprost. Approximately one drop of XALATAN™ solution contains about 1.5 μg of latanoprost.

Latanoprost, as the active ingredient in the XALATAN™ ophthalmic solution, is conventionally used to reduce elevated intraocular pressure in patients with glaucoma and ocular hypertension.

When latanoprost is used in the method of the present invention, such a preparation may be made up by using XALATAN™ as the melanogenesis agent. The XALATAN™ preparation is applied topically to the affected eye or eyes once daily at a dosing level of approximately one drop (about 1.5 μg of latanoprost) to approximately three drops (about 4.5 μg of latanoprost) per day per eye for the 0.005% solution. This dosage range is applicable to each of the three following stages of macular degeneration, namely: early onset macular degeneration, atrophic macular degeneration (dry), and neovascular macular degeneration (wet).

It is contemplated that the dosing levels of latanoprost as used in the present invention would be adjusted as necessitated by lack of response, speed of response needed, strength of latanoprost solution, etc.

The method of the present invention may be practiced alone or in conjunction with other therapy.

In more than 50% of cases where age-related macular degeneration occurs in one eye, it will occur in the other eye within one year. Prophylactic administration of prostaglandin F$_{2\alpha}$ derivatives may be useful in such cases.

EXAMPLE

In an example of treatment according to the preferred embodiment described above, a male patient aged 64 with blue eyes was diagnosed with age-related macular degeneration of about ten years' duration. Numerous druscen were documented in both eyes. Photographs of the fundus were obtained. Treatment with latanoprost according to the preferred method of use described herein was initiated in the left eye. After two months of treatment, pigment spots were observed in the iris of the treated eye. After two years of treatment, changes in hair color of eyelashes and head hair from gray to pigmented have also been noted, indicating that the latanoprost is having a systemic melanogenistic effect. After two years of treatment, the treated eye showed no changes in visual acuity from that measured at the start of treatment. There were also no changes in the fundus, such as increases in the number or extent of the druscen, compared with the photographs obtained before the start of treatment. Thus, treatment with latanoprost according to the methods of the present invention has prevented any additional effects from macular degeneration from occurring in the treated eye. This is significant because, as described above, the normal course of macular degeneration leads to a continuous, on-going loss of vision over time.

The above disclosure sets forth an embodiment of the present invention. Other arrangements or embodiments, not precisely set forth, could be practiced under the teachings of the present invention.

I claim:

1. A method of treating macular degeneration in an eye, said method comprising contacting said eye with a therapeutically effective amount of a prostaglandin $F_{2\alpha}$ derivative.

2. The method of claim 1 wherein said prostaglandin $F_{2\alpha}$ derivative has the formula 13,14-dihydro-15(R)-17-phenyl-18,19,20-trinor-$PGF_{2\alpha}$ isopropyl ester:

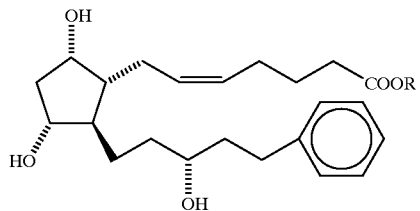

wherein R is a saturated or unsaturated straight, branched, or cyclic $C_{1-7}$ alkyl or phenyl or benzyl group.

3. The method of claim 1 wherein said prostaglandin $F_{2\alpha}$ derivative is latanoprost:

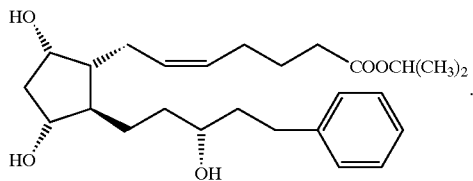

4. The method of claim 1 wherein the dosage of prostaglandin $F_{2\alpha}$ derivative is between about 1.5 μg and about 4.5 μg per day.

5. A method of treating macular degeneration in an eye, said method comprising contacting said eye with a therapeutically effective amount of a prostaglandin $F_{2\alpha}$ derivative having the formula 13,14-dihydro-15(R)-17-phenyl-18,19,20-trinor-$PGF_{2\alpha}$ isopropyl ester:

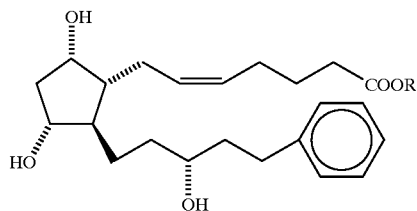

wherein R is a saturated or unsaturated straight, branched, or cyclic $C_{1-7}$ alkyl or phenyl or benzyl group.

6. The method of claim 5 wherein said prostaglandin $F_{2\alpha}$ derivative is latanoprost:

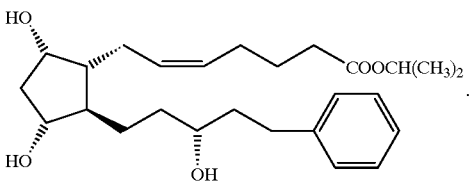

7. The method of claim 5 wherein the dosage of prostaglandin $F_{2\alpha}$ derivative is between about 1.5 μg and about 4.5 μg per day.

8. A method of treating macular degeneration in an eye, said method comprising contacting said eye with a dosage of a prostaglandin $F_{2\alpha}$ derivative between about 1.5 μg and about 4.5 μg per day, said prostaglandin $F_{2\alpha}$ derivative having the formula 13,14-dihydro-15(R)-17-phenyl-18,19,20-trinor-$PGF_{2\alpha}$ isopropyl ester:

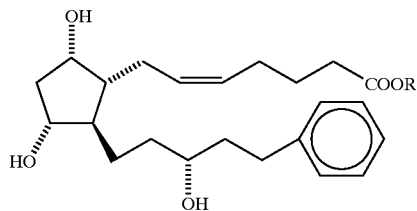

wherein R is a saturated or unsaturated straight, branched, or cyclic $C_{1-7}$ alkyl or phenyl or benzyl group.

9. The method of claim 8 wherein said prostaglandin $F_{2\alpha}$ derivative is latanoprost:

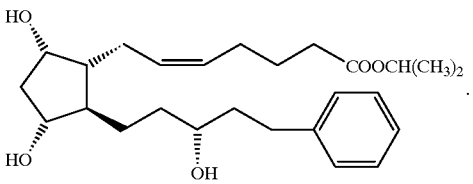

* * * * *